United States Patent [19]

Mason et al.

[11] 4,181,718

[45] Jan. 1, 1980

[54] POLYANION-STABILIZED ALUMINUM HYDROGELS

[76] Inventors: Norbert S. Mason, 725 Langton Dr., Clayton, Mo. 63105; Robert E. Sparks, 1318 W. Adams Ave., Kirkwood, Mo. 63122

[21] Appl. No.: 877,504

[22] Filed: Feb. 13, 1978

Related U.S. Application Data

[63] Continuation of Ser. No. 645,100, Dec. 29, 1975, abandoned, which is a continuation-in-part of Ser. No. 560,220, Mar. 20, 1975, abandoned, which is a continuation-in-part of Ser. No. 331,151, Feb. 9, 1973, abandoned.

[51] Int. Cl.$^2$ ............... A61K 31/715; A61K 31/725; A61K 33/06
[52] U.S. Cl. ............................. 424/180; 424/78; 424/79; 424/154; 424/157; 424/158; 424/177
[58] Field of Search ............... 424/79, 154, 157, 158, 424/180, 78, 177

[56] References Cited

U.S. PATENT DOCUMENTS

| | | | |
|---|---|---|---|
| 3,175,942 | 3/1965 | Anderson et al. | 424/158 |
| 3,326,755 | 6/1967 | Sheth | 424/180 |
| 3,364,111 | 1/1968 | Morii et al. | 424/154 |
| 3,555,151 | 1/1971 | Kaplan et al. | 424/157 |
| 3,579,634 | 5/1971 | Brown | 424/158 |

*Primary Examiner*—Sam Rosen
*Attorney, Agent, or Firm*—Gerald D. Sharkin; Robert S. Honor; Walter F. Jewell

[57] ABSTRACT

Aluminum hydrogels which are stabilized at pH below 7 with a polymer containing carboxyl groups, e.g., carboxy methyl cellulose or gum arabic. The gels are useful as phosphate binding agents in the treatment of hyperphosphatemia. Such polymers are incorporated during the formation of the aluminum hydrogel, permitting a high yield to be obtained, and preventing colloidal sol formation during exchange with monovalent anions.

15 Claims, No Drawings

POLYANION-STABILIZED ALUMINUM HYDROGELS

The invention described herein was made in the course of work under a grant or award from the Department of Health, Education and Welfare.

This application is a continuation of application Ser. No. 645,100, filed Dec. 29, 1975, now abandoned, which in turn is a continuation-in-part of application Ser. No. 560,220, filed Mar. 20, 1975, now abandoned, which in turn is a continuation-in-part of Ser. No. 331,151, filed Feb. 9, 1973, now abandoned.

This invention relates to aluminum hydrogels. More particularly, it relates to aluminum hydrogels formed at pH below 7 in the presence of a carboxy-containing polymer and to their use as phosphate binding agents, particularly as phosphate binding agents in the treatment of hyperphosphatemia.

Hyperphosphatemia may be treated by removal of phosphorous from a patient by binding phosphates in the intestinal tract. The prior art phosphate binding agents an antacid hydrated hydrogels, e.g., aluminum carbonate gel, which are insoluble in water or acids and remove phosphate by ion exchange. In pharmaceutically available form the hydrogels are partially dehydrated with a resultant loss in original phosphate binding capacity. Because this dehydration is irreversible, these materials cannot be rehydrated to recover this capacity. This is particularly a problem when these prior art gels are used in tablet form, wherein phosphate capacity can be irreversibly decreased by a factor of six. These prior art gels are also so astringent in taste that it is difficult for a patient to take the amount of gel required to maintain a phosphorous balance.

It is, therefore, an object of this invention to prepare aluminum hydrogels which have a high phosphate capacity and which maintain a high phosphate capacity upon dehydration and which are basically non-astringent.

The novel phosphate-binding agents of this invention are aluminum hydrogels formed at pH below 7 in the presence of polymeric anions. Broadly, they may be prepared by the addition of a large anion, e.g., 1000 to 700,000 molecular weight, particularly a high molecular weight hydrophilic anionic polymer to an aluminum salt either before neutralization of the aluminum salt or during its subsequent exchange with solutions containing monovalent ions which would otherwise solubilize most of the gel. Hence, the polyanion stabilizes the gel, permitting it to be obtained in high yield in the dilute solutions which are necessary to obtain gels having high phosphate binding capacity, by the addition of a large anion, particularly a high molecular weight anionic polymer to an aluminum salt either during its subsequent exchange with solutions containing monovalent ions which would otherwise solubilize most of the gel. Hence, the polyanion stabilizes the gel, permitting it to be obtained in high yield in the dilute solutions which are necessary to obtain gels having high capacity.

The aluminum hydrogels of this invention may be prepared by the following methods:

Methods A, B, and C can be used when the anion in the aluminum salt, e.g., $SO_4^{-2}$ is undesirable pharmaceutically and is exchanged for a pharmaceutically acceptable anion, e.g., acetate ion.

(A) an aluminum salt, e.g., $Al_2SO_4$ is neutralized in an aqueous medium containing a stabilizing polyanion, e.g., gum arabic, followed by washing and separation of the resulting gel by conventional techniques, e.g., centrifugation. The anion, e.g., $SO_4^{-2}$, is then exchanged in an aqueous acid solution, e.g., acetic acid for the corresponding acid ion, e.g., acetate ion. After the ion exchange, conventional washing and separating techniques are used to separate the gel;

(B) The procedure of Method A is followed except that the polyanion is added before the ion exchange step of the aluminum salt and the resulting polyanion stabilized gel is then ion exchanged and recovered as described in Method A;

(C) The procedure of Method A is followed except that the polyanion is added during the ion exchange step, and the resulting stabilized gel is recovered as described in Method A;

Methods D and E may be used when the starting material contains a pharmaceutically acceptable anion, e.g., tartrate ion, and therefore, no ion exchange step is necessary.

(D) The procedure of Method A is followed except that the ion exchange step is omitted and the gel recovered as described in Method A; and (E) The procedure of Method B is followed except that the ion exchange step is omitted and the gel recovered as described in Method B.

Both the inorganic and organic salts of aluminum such as $NaAlO_2$, $Al_2(SO_4)_3$, $Al(NO_3)_3$, $AlCl_3$, aluminum lactate, aluminum tartrate and the like, may be used in the preparation of aluminum hydrogels. The preferred salts are $Al(SO_4)_3$, $NaAlO_2$ and $AlCl_3$. $Al(SO_4)_3$ is especially preferred.

The neutralization may be carried out at a pH of from 3.5 to 7.0, preferably at pH 4.0 to 7.0. Among the neutralization agents that may be utilized to generate the gel when an acidic aluminum salt, e.g., $Al(SO_4)_3$ is used are bases, such as $NH_4OH$, $NaOH$, $Na_2CO_3$ and the like, with $NH_4OH$ being preferred. When a basic aluminum salt, e.g., $NaAlO_2$ is used, acidic neutralization agents, such as sulfuric acid, hydrochloric acid, acetic acid, L-ascorbic acid, propionic acid, malonic acid, ethylene maleaic anhydride, $CO_2$, methylvinylether-maleic anhydride copolymer, and the like, may be utilized with sulfuric acid, acetic acid, L-ascorbic acid and ethylene maleic anhydride being preferred.

When an aluminum salt, e.g., $Al_2(SO_4)_3$ containing an anion, e.g., $SO_4^{-2}$ which is undesirable in a pharmaceutically acceptable gel is used, the ion may be exchanged. The undesirable ion may be exchanged with acetate ion, carbonate ion, tartrate ion, citrate ion, succinate ion, fumarate ion, glutarate ion, glutamate ion, or aspartate ion. The ion exchange may be carried out in from about a 0.1 molar solution to a saturated solution, preferably 0.5 molar solution to 1 molar solution of acetic acid, tartaric acid, citric acid, succinic acid, fumaric acid, glutaric acid, glutamic acid, or aspartic acid, or a salt thereof made acidic to pH 4.5 to 6 with the corresponding acid, to yield the corresponding aluminum salt. The preferred exchange material is acetic acid or sodium acetate-acetic acid. The ion exchange may be carried out at a pH from 4 to 7.0, preferably pH 4 to 7, and especially at pH 5.5 to 6.0.

Alternately, the undesirable sulfate ion can be removed by precipitation before generating the gel. This may be done by adding a calcium salt to precipitate the sulfate keeping the pH below 4 to keep the aluminum ion in solution. Calcium sulfate may be filtered off. The aluminum gel can then be precipitated by the methods of D and E, the polyanion being added after precipitation of the sulfate ion. The calcium salt can be supplied with the desired pharmacological ion.

Among the anionic polymers that may be added during the gel formation are carboxymethyl callulose, (having a molecular weight range of 5000 to 700,000, preferably 80,000 to 700,000 and a degree of substitution of 0.4 to 1.5, preferably 0.5 to 1.2) gum arabic; gelatin (having a molecular weight range of 15,000 to 250,000, and an isoelectric point of 4.7–5;), ethylene maleic anhydride co-polymer (having a molecular weight range of 1000 to 100,000, preferably, 60,000 to 90,000), and the like. Gum arabic and carboxy methyl cellulose are the preferred hydrophilic polymers.

That stabilized gel of this invention may contain from about 1 to 80 percent of the anionic polymer based on the weight of the gel.

The phosphate binding agents prepared by Methods A, B, C, D, or E may be suitably dried for use in solid pharmaceutical forms, e.g., tablets or capsules, by conventional techniques, e.g., spray drying, vacuum drying, or freeze drying.

The phosphate binding agents of this invention may be used in the treatment of hyperphosphatemia in the form of oral liquid suspension as tablets, capsules, or as a powder. In the drying step, it was found necessary for maintenance of the gel effectiveness to avoid agglomeration of the small primary particles. The desired particle size of spherical particles is less than 50 microns with the preferred particle size below 35 microns. Dosages suitable for treating hyperphosphatemia will vary depending on the severity of the condition being treated, however, satisfactory results are obtained when the active agent is given to large mammals, e.g., primates, at a total daily dosage of from 1.0 grams to about 20 grams.

EXAMPLE 1

To a liter beaker equipped with an air driven turbine agitator was added 165 grams $Al_2SO_4.18H_2O$ and 3000 milliliters of deionized water. The mixture was agitated to dissolve the aluminum salt. A pH meter electrode was mounted in the solution to continuously monitor pH. The pH of the solution was quickly raised to pH 4.5 with concentrated amonium hyroxide and further neutralized slowly to pH 5.5 with 1.0 N ammonium hydroxide. The thus neutralized gel was then removed from the beaker and centrifuged for 5 minutes at 2000 g's in a laboratory batch centrifuge. The clear supernatant liquid was discarded and the gel redispersed in 3000 milliliters of deionized water.

The dispersion was then centrifuged for 10 minutes at 2000 times the force of gravity (g's) with the clear supernatant liquid again discarded and the gel again redispersed in 3000 milliliters of deionized water. The resulting dispersion was again centrifuged for 10 minutes at 2000 g's, and the supernatant liquid again discarded. The gel was redispersed in 1500 milliliters of 0.5 M sodium acetate-acetic acid solution of pH 5.6. After one hour, 7.8 grams of gum arabic dissolved in 100 milliliters of deionized water was added with agitation to the dispersion. The resulting suspension was then centrifuged for 45 minutes at 2000 g's. The clear supernatant liquid was discarded and the resulting gel dispersed in 5 liters of deionized water. The resulting suspension was then centrifuged for 15 minutes at 2000 g's. The clear supernatant liquid was again discarded and the gel dispersed in 5 liters of deionized water and the suspension centrifuged for 15 minutes at 2000 g's.

The sulfate ion ($SO_4^{-2}$) content of the supernatant liquid was determined by adding $BaCl_2$ crystals to 5 milliliters of the supernatant liquid and comparing the resulting turbidity to sodium sulfate solutions containing 25 ppm and 100 ppm of $SO_4^{-2}$. The supernatant liquid contained less than 25 ppm $SO_4^{-2}$.

The yield of the wet gel was 400 grams. (8.8 percent solids).

The phosphate ion capacity of the aluminum hydrogel was determined by adding the amounts of wet gel shown in Table I to centrifuge tubes containing 40 milliliters of a solution of phosphate ion buffered at pH 7. After the gel addition, the tubes were capped and shaken in a water bath at 38° C., for 24 hours, and then centrifuged for 15 minutes. The supernatant liquid and the original solution was analyzed for phosphate according to the method of G. Fomori, "A Modification of Colorimetric Phosphorous Determination for Use With the Photoelectric Colorimeter", J. Lab. Clin. Med. 27, 955 (1942).

TABLE I

| No. | Wet-Gel Added (Grams) | Gel-Dry Basis[1] (Grams) | Conc. $PO_4$[2] mg/100 ml. | Gel $PO_4$ capacity mg $PO_4$ Gram dry gel |
|---|---|---|---|---|
| 1. | 1.49 | 0.139 | 279 | 664 |
| 2. | 3.26 | 0.305 | 138 | 487 |
| 3. | 4.71 | 0.441 | 42 | 425 |

[1] Moisture evaporation at 25 in. mercury vacuum at 100° C. until constant weight (6 to 24 hours).
[2] In the supernatant liquid.

EXAMPLE 2

The aluminum hydrogel of Example 1 was frozen in refrigerator ice-cube trays, and then crushed and placed in a lyophilizer and freeze dried. The gel was dried to 70 percent solids (as measured by comparison to drying in a vacuum oven). The resulting gel was a fine white powder which was insoluble in water and 0.1 N HCl. The phosphate ion capacity of the freeze-dried gel was determined as described in Example 1. The results are shown in Table II.

Different methods of drying were compared. Drying in static air in an oven at 78° C. gave a gel having a capacity of 46.2 percent of that of freeze-dried gel. On the other hand, spray drying and drying in a thin film on a heated drum gave a gel having substantially the capacity as that of the freeze dried material.

TABLE II

| | | | | Gel $PO_4$ capacity mg. $PO_4$ Grams Dry Gel | |
|---|---|---|---|---|---|
| No. | Freeze-Dried Gel (Grams) | Oven-Dried Basis[1] (Grams) | Conc. $PO_4$[2] mg/100 ml. | Freeze Dried Basis | Oven[3] Dried Basis |
| 1. | 0.226 | 0.159 | 300 | 252 | 360 |
| 2. | 0.599 | 0.420 | 105 | 225 | 323 |
| 3. | 0.661 | 0.468 | 76.5 | 222 | 316 |
| 4. | 1.04 | 0.730 | 0.9 | 169 | 243 |

[1] Moisture evaporation at 25 in. mercury vacuum at 100° C. until constant weight (6 to 24 hours).
[2] In the supernatant liquid.
[3] Results are based on measurements of the freeze-dried gel. The oven-dried weight being used in the calculation of this column.

EXAMPLE 3

An aluminum hydrogel was prepared as described in Example 1 without the addition of gum arabic. The $Al_2(SO_4)_3$ sodium acetate-acetic acid solution was centrifuged at 2000 g's for one hour without producing a clear supernatant liquid. The solids were dispersed in 5 liters of deionized water and centrifuged at 2000 g's for one hour with a resulting turbid supernatant liquid. The solids were again dispersed in 5 liters of deionized water and centrifuged at 2000 g's for one hour. The supernatant liquid from the first wash contained 0.7 percent solids. These solids did not settle out after one month, indicating that stable sols were formed. The liquid contained more than 100 ppm of $SO_4^{-2}$. The second supernatant liquid was turbid and contained 25 pp of $SO_4^{-2}$. (It is to be noted that $BaSO_4$ can be distinguished from hydrous aluminum oxide sol turbidity, as the latter is bluish and remains suspended while the former is white and settles out rapidly). This demonstrates the stabilizing effect of the polyanion.

EXAMPLE 4

To a 4 liter beaker equipped with an air driven turbine agitator was added 300 milliliters of a 0.1 N aluminum sulfate solution. One-hundred milliliters of a 2.2 percent carboxymethyl cellulose solution was added with stirring. A pH meter electrode was mounted in the solution to continuously monitor pH. The pH of the solution was raised to pH 4.5 with concentrated ammonium hydroxide, and then raised to pH 5.5 with 1.0 normal ammonium hydroxide. The resulting gel was washed with deionized water containing 2.2 grams of carboxymethyl cellulose and then centrifuged for 5 minutes at 2000 g's in a laboratory batch centrifuge. The clear supernatant liquid was discarded and the remaining gel was redispersed in 3000 milliliters of deionized water containing 2.2 percent of carboxymethyl cellulose. The dispersion was then centrifuged for 10 minutes at 2000 g's with the clear supernatant liquid again discarded and the resulting gel again redispersed in 3000 milliliters of deionized water containing 2.2 percent carboxymethyl cellulose. The resulting dispersion was again centrifuged for 10 minutes at 2000 g's, and the supernatant liquid again discarded. The resulting gel was redispersed in 1500 milliliters of 0.5 M sodium acetate-acetic acid solution of pH 5.6 containing 2.2 percent carboxymethyl cellulose. After one hour, 7.8 grams of gum arabic dissolved in 100 milliliters of deionized water was added with agitation to the dispersion. The resulting suspension was then centrifuged for 45 minutes at 2000 g's. The clear supernatant liquid was discarded and the resulting gel dispersed in 5 liters of deionized water. The resulting suspension was then centrifuged for 15 minutes at 2000 g's. The clear supernatant liquid was again discarded and the gel dispersed in 5 liters of deionized water and the suspension centrifuged for 15 minutes at 2000 g's. The resulting gel had a phosphate binding capacity of 402 milligrams $PO_4$ per gram of dry gel and the supernatant liquid had a final concentration of 240 milligrams $PO_4/100$ milliliters, when tested by the procedure of Example 1.

EXAMPLE 5

Starting with 40 milliliters of 0.1 N $AlCl_3$ solution to which 1 milliliter of a 2.2 percent gelatin solution was added, the neutralization and washing procedures of Example 4 were followed. The resulting wet gel was oven dried to a 178.3 grams residue, containing 44.7 milligrams $PO_4$.

When the above procedure was folllowed but without the gelatin, only 31.1 milligrams of dried gel was obtained. This indicates that the polyanion enters directly into the gel formation, acting as a stabilizing bridging anion.

EXAMPLE 6

To 35 gallons of deionized water in a polyethylene coated drum equipped with an agitator was added 2750 grams of $Al_2SO_4.H_2O$, and the mixture was agitated to dissolve the aluminum salt. A pH meter electrode was mounted in the solution to continuously meter pH. The solution was neutralized to pH 5.5 with 1.0 N ammonium hydroxide. The resulting gel was separated in a 12-inch diameter solid-bowl Tollhurst continuous centrifuge at 2100 RPM. The gel was consequently washed twice and again separated by centrifugation in the Tollhurst centrifuge at 2500 RPMs. The gel was then mixed for one hour with 0.5 M sodium acetate made acidic with acetic acid to pH 5.7. The resulting gel could no longer be separated by the centrifuge even at dropwise rates of addition. Sixty grams of gum arabic dissolved in one gallon of deionized water was then added to the sodium acetate gel suspension and allowed to agitate for 15 minutes. The resulting gel was easily separated by centrifuge.

The difficulty in separating the gel prior to the addition of the gum arabic is an indication that the polyanion enters into the gel formation, providing a gel which is easily separated from the solution from which it is formed.

EXAMPLE 7

To a liter beaker equipped with an air driven turbine agitator was added 165 grams $Al_2SO_4.18H_2O$ and 3000 milliliters of deionized water. The mixture was agitated to dissolve the aluminum salt. A pH meter electrode was mounted in the solution to continuously monitor pH. The pH of the solution was quickly raised to pH 4.5 with concentrated ammonium hydroxide and further neutralized slowly to pH 5.5 with 1.0 N ammonium hydroxide. The thus neutralized gel was then removed from the beaker and centrifuged for 5 minutes at 2000 g's in a laboratory batch centrifuge. The clear supernatant liquid was discarded and the gel redispersed in 3000 milliliters of deionized water. The dispersion was then centrifuged for 10 minutes at 2000 times the force of gravity (g's) with the clear supernatant liquid again discarded and the gel again redispersed in 3000 milliliters of deionized water. The resulting dispersion was again centrifuged for 10 minutes at 2000 g's and the supernatant liquid again discarded. 7.8 grams of gum arabic dissolved in 100 milliliters of deionized water was added with agitation to a 3000 milliliter dispersion of the gel. After one hour, the gel was redispersed in 1500 milliliters of 0.5 M sodium acetate-acetic acid solution of pH 5.6. The resulting suspension was then centrifuged for 45 minutes at 2000 g's. The clear supernatant liquid was discarded and the resulting gel dispersed in 5 liters of deionized water. The resulting suspension was then centrifuged for 15 minutes at 2000 g's. The clear supernatant liquid was again discarded, and the gel dispersed in 5 liters of deionized water and the suspension centrifuged for 15 minutes at 2000 g's to recover the gel.

EXAMPLE 8

Following the procedure of Example 1, 165 grams of aluminum tartrate was dissolved in 3000 milliliters of deionized water. The solution was neutralized to pH 5.5 with 1.0 N ammonium hydroxide. The thus neutralized gel was twice washed and centrifuged as described in Example 1, and the resulting gel was dispersed in 3000 milliliters of deionized water. 7.8 grams of gum arabic dissolved in 100 milliliters of deionized water was then added with agitation to the dispersion. After being washed twice and centrifuged twice, the gel was recovered.

EXAMPLE 9

Following the procedure of Example 4, 165 grams of aluminum tartrate was dissolved in 3000 milliliters of deionized water. To the resulting solution was added 7.8 grams of gum arabic dissolved in 100 milliliters of deionized water. The resulting mixture was agitated and then neutralized to pH 5.5 with 1.0 N ammonium hydroxide. The resulting gel was collected after being twice washed and centrifuged as described in Example 4.

EXAMPLE 10

The following formulation for a liquid oral suspension containing an effective amount of the active compound may be formulated using conventional methods. The formulation is useful in treating hyperphosphatemia.

| | |
|---|---|
| Gum arabic-stabilized aluminum hydrogels (ex. 1) | 100 grams |
| peppermint oil | 0.01 grams |
| sodium benzoate | 0.1 grams |
| water | q.s. |

EXAMPLE 11

Tablets suitable for administration which contain the following ingredients may be prepared by conventional tabletting techniques. Such tablets are useful in treating hyperphosphatemia.

| Ingredients | Weight (Mg.) |
|---|---|
| Gum arabic-stabilizing aluminum hydrogels (ex. 1) | 500 |
| tragacanth | 10 |
| lactose | 100 |
| corn starch | 25 |
| talcum | 15 |
| magnesium stearate | 2.5 |

EXAMPLE 12

Capsules suitable for oral administration which contain the following ingredients are prepared in a conventional manner. Such capsules are useful in treating hyperphosphatemia.

| Ingredients | Weight (Mg.) |
|---|---|
| Gum arabic-stabilizing aluminum hydrogel (ex. 1) | 500 |
| inert solid diluent (starch, lactose, kaolin) | 200 |

EXAMPLE 13

The effectiveness of the novel polyanion-stabilized aluminum hydroxide of this invention was tested in six dogs. The animals were placed on 1200 milligrams phosphorous (inorganic phosphate) diet for three weeks. At the end of this time period, the dogs were fasted for 18 hours and phosphorous levels in urine and blood serum were measured. Each animal was then given 15 milligrams phosphorous (as an inorganic phosphate) per pound of body weight, via a gastric tube and the urine and blood serum phosphate was measured for a period of five hours. The phosphorous level in the blood plasma increased to a peak value 9.6 milligrams per 100 milligrams with 70 percent of the original phosphorous intake recovered in the urine.

After a one week interval, the animals were again placed on a 1200 milligram phosphorous diet for three weeks. At the end of the period, the dogs were fasted for 18 hours and urine and blood serum phosphate was measured. Each animal was given 15 milligrams of phosphorous per pound of body weight, via a gastric tube. After five minutes, one-half of the animals were given 25 milliliters of aluminum carbonate gel (BASALJEL-Wyeth Laboratories) and the other half of the animals given the dry weight equivalent of the polyanion-stabilized aluminum hydroxide of Example 1. When BASALJEL was given, the blood serum phosphorous increased to 5.5 milligrams per 100 milliliters and 43 percent of the oral dosage appeared in the urine. However, when the polyanion-stabilized aluminum hydroxide of Example 1 was given, the blood serum phosphorous increased only to 4.5 milligrams per 100 milliliters and only 25 percent of the oral dosage appeared in the urine.

This indicates that the polyanion-stabilized aluminum hydroxide of the present invention is more effective than the commercial gel in binding phosphate.

EXAMPLE 14

Preparation of Phosphorous Binder—Bread Sticks

Materials
  Aluminum Sulfate Anhydrous (USP) 7.5 kilograms
  Glacial Acetic Acid J. T. Baker 3-9507 15.6 kilograms
  Calcium Carbonate USP 13.1 kilograms
  Carbonate of soda monohydrate USP 7 kilograms
  Carboxymethyl cellulose type 7 MF 200 grams (CMC)

Equipment
  2 polyethylene lined 55 gallon drums equipped with stainless steel mixing blades and cover;
  1 perforated bowl centrifuge equipped with a porous polyethylene liner;
  2 peristalic pumps; and
  1 deionizer Procedure Aluminum sulfate was dissolved in 25 gallons deionized water. Acetic acid, then calcium carbonate were added. The precipitated calcium sulfate was removed by centrifugation and discarded.

To the clear liquid was added sufficient sodium carbonate solution (7.0 kilograms dissolved in 8 gallons of deionized water) to bring the pH to 6.1. The suspension was then passed through the centrifuge to recover part of the aluminum gel. The supernatant was pumped to the second drum and 100 grams of carboxymethyl cellulose dissolved in 2 gallons was added with mixing. The precipitate was allowed to settle and was then pumped through the centrifuge again.

When all the precipitate was recovered it was weighed, sampled for analysis and redispersed in 30 gallons of deionized water to remove the free ions. This washing step was repeated three times, the precipitate being weighed and sampled for analysis at each step.

Formulation and Results

Analytical results are shown on Table III. Batches 2 and 3 were mixed and spray dried. After spray drying the batches were formulated into bread sticks by blending the phosphate binder in standard commercial dough forming the dough into bread sticks and baking the sticks in a conventional manner.

The bread sticks were tested for phosphorous up take. The results from these tests showed that 14 grams of bread sticks containing 7.3 percent binder removed 104.5±5.5 milligrams phosphorous from 250 milliliters of an aqueous solution containing origianlly 77.4±0.90 milligrams per 100 milliliters of solution (N=4). Bread sticks which had no binder removed no phosphorous from the solution. Taste could not differentiate between the bread sticks containing 7.4 percent binder and those not containing binder.

TABLE III

| Batch | SO4 % | | | Na % | | | Ca % | | | Al % | | | P capacity (mg/gm) (final conc., mg %) | | |
|---|---|---|---|---|---|---|---|---|---|---|---|---|---|---|---|
| | 1 | 2 | 3 | 1 | 2 | 3 | 1 | 2 | 3 | 1 | 2 | 3 | 1 | 2 | 3 |
| Nascent Gel | 0.85 | 0.51 | .39 | 5.4 | 7.2 | 6.9 | 8.0 | 10.2 | 11.3 | | | | | 107.7 (18.9) | 115.9 (13.2) |
| After 1st wash | 1.07 | 0.52 | .59 | 1.6 | 2.3 | 1.7 | 7.7 | 9.3 | 11.5 | | | | | 115.4 (15.4) | 120.9 (21.1) |
| After 2nd wash | 1.36 | 0.70 | .45 | 0.4 | 0.32 | 0.29 | 6.8 | 8.5 | 11.3 | | | | | | 119.7 (20.9) |
| After 3rd wash | 1.44 | 0.69 | .45 | 0.0 | 0.12 | 0.17 | 6.0 | 6.9 | 11.9 | | | | 113.7 (5.5) 124 (10.6) | 108.8 (18.7) 113.1 (30.7) | 107.8 (29) |
| After freeze drying | | | | | | | | | | | | | 91.2 (45.2) | 84.1 (34.9) | 62.09 (40.8) |
| After spray drying | | | | | | | | | | 23.56* | 21.72** | | 96.9 (58.2) | 81.3 (45.5) 74.4 (56.2) | |

*moisture 6.23 percent
**moisture 8.24 percent
All analyses based upon vacuum oven-dried weight (100° C. 28 in Hg for 18 hours).

What is claimed is:

1. A non-astringent phosphate binding agent having a high phosphate binding capacity which capacity is maintained upon dehydration comprising a stabilized hydrogel of an aluminum salt and a carboxy-containing polymeric anion having a molecular weight of from 1,000 to 700,000, with the hydrogel formed at a pH below about 7.

2. The phosphate binding agent of claim 1 wherein the aluminum salt is aluminum acetate and the polymeric anion is selected from the group consisting of gum arabic and carboxymethyl cellulose.

3. A method of preparing the phosphate binding agent of claim 1, which comprises neutralizing an aluminum salt at a pH of from 3.5 to 7.0 to form an aluminum hydrogel, exchanging the anion of the aluminum hydrogel with a pharmaceutically acceptable anion in the presence of the stabilizing polymeric anion.

4. The method of claim 3, wherein the neutralization pH range is from pH 4.0 to 7.0.

5. A method of preparing the phosphate binding agent of claim 1, which comprises neutralizing a mixture of an aluminum salt and a polymeric anion at a pH of from 3.5 to 7.0, to form an aluminum hydrogel stabilized by the polymeric anion, and subsequently exchanging the anion of the stabilized alumiunum hydrogel with a pharmaceutically acceptable anion.

6. The method of claim 5, wherein the neutralization pH range is from pH 4.0 to 7.0.

7. A method of preparing the phosphate binding agent of claim 1, which comprises neutralizing an aluminum salt at a pH of 3.5 to 7.0, to form an aluminum hydrogel in the presence of the polymeric anion, and subsequently exchanging the anion of the aluminum hydrogel with a pharmaceutically acceptable anion.

8. The method of claim 7, wherein the neutralization pH range is from pH 4.0 to 7.0.

9. A method of preparing the phosphate binding agent of claim 1, which comprises partially neutralizing an aluminum salt at a pH of from 3.5 to 7.0, to form an aluminum hydrogel, and subsequently completely neutralizing the aluminum hydrogel in the presence of the stabilizing polymeric anion.

10. The method of claim 9, wherein the neutralization pH range is from pH 4.0 to 7.0.

11. A method of preparing the phosphate binding agent of claim 1, which comprises neutralizing a mixture of an aluminum salt and the polymeric anion at a pH of from 3.5 to 7.0, to form an aluminum hydrogel, with a polymeric anion.

12. The method of claim 11, wherein the neutralization pH range is from pH 4.0 to 7.0.

13. A method of treating hyperphosphatemia, which comprises administering to a mammal in need of such treatment a hyperphosphatemic effective amount of a phosphate binding agent of claim 1.

14. The method of treating hyperphosphatemia according to claim 13, wherein the phosphate binding agent is administered in the form of a tablet.

15. The method of treating hyperphosphatemia according to claim 13, wherein the phosphate binding agent is administered in the form of a bread stick.

* * * * *